(12) United States Patent
Masaoka

(10) Patent No.: US 7,160,509 B2
(45) Date of Patent: Jan. 9, 2007

(54) METHOD OF STERILIZATION AND APPARATUS THEREFOR

(75) Inventor: Satoshi Masaoka, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 0 days.

(21) Appl. No.: 10/493,585

(22) PCT Filed: Sep. 9, 2003

(86) PCT No.: PCT/JP03/11520

§ 371 (c)(1),
(2), (4) Date: Apr. 23, 2004

(87) PCT Pub. No.: WO2004/024566

PCT Pub. Date: Mar. 25, 2004

(65) Prior Publication Data

US 2005/0053520 A1 Mar. 10, 2005

(30) Foreign Application Priority Data

Sep. 10, 2002 (JP) .............................. 2002-264012

(51) Int. Cl.
*A61L 2/16* (2006.01)

(52) U.S. Cl. .................. 422/28; 422/292; 422/304; 141/85; 53/425

(58) Field of Classification Search ............... 422/3, 422/28, 105, 292, 304; 141/85, 89; 53/425
See application file for complete search history.

(56) References Cited

U.S. PATENT DOCUMENTS 5,997,294 A * 12/1999 Declercq ................ 432/224
6,481,468 B1 * 11/2002 Taggart ................... 141/85
6,537,491 B1 * 3/2003 Wang et al. ............... 422/3
2002/0083682 A1* 7/2002 Edwards et al. ........... 53/426

FOREIGN PATENT DOCUMENTS

| EP | 0758611 | 2/1997 |
|----|---------|--------|
| EP | 0842877 | 5/1998 |
| JP | 2000-326935 | 11/2000 |
| JP | 2001-039414 | 2/2001 |
| JP | 2001116611 | 4/2001 |
| JP | 2001116611 A * | 4/2001 |
| JP | 2003-231510 | 8/2003 |
| WO | WO9930747 | 6/1999 |

* cited by examiner

*Primary Examiner*—Gladys J P Corcoran
*Assistant Examiner*—Sean Conley
(74) *Attorney, Agent, or Firm*—Ladas & Parry LLP

(57) ABSTRACT

A liquid germicide is measured; the measured liquid germicide is injected into hollows of concave articles (1); the more or less of volume of the liquid germicide is discriminated from the injected liquid germicide; only concave articles (1) which each have a proper volume of the liquid germicide attached thereto are stored into a storage (6); thereafter the storage is closed, and the concave articles are left to stand in the closed storage for a prescribed period of time. Since the liquid germicide is injected into the hollow of the concave article (1) after measuring, and the more or less of volume of the solution is discriminated from the injected liquid germicide as described above, it is possible to attach a proper amount of liquid germicide to concave article (1) such as vessel or preform, and hence to accomplish efficient sterilization in the storage (6), without the risk of the defective sterilization.

7 Claims, 9 Drawing Sheets

FIG. 1A
FIG. 1B
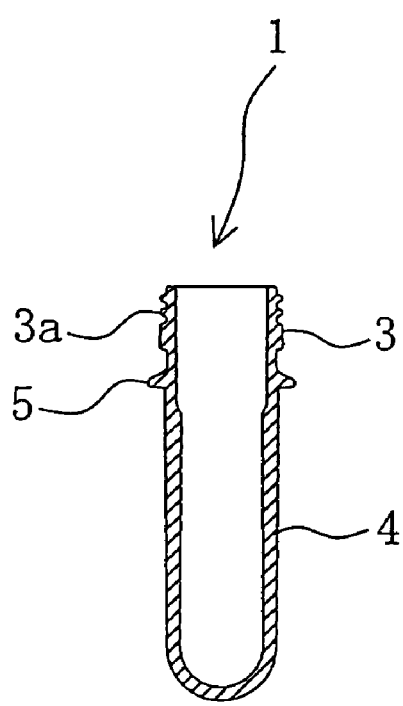
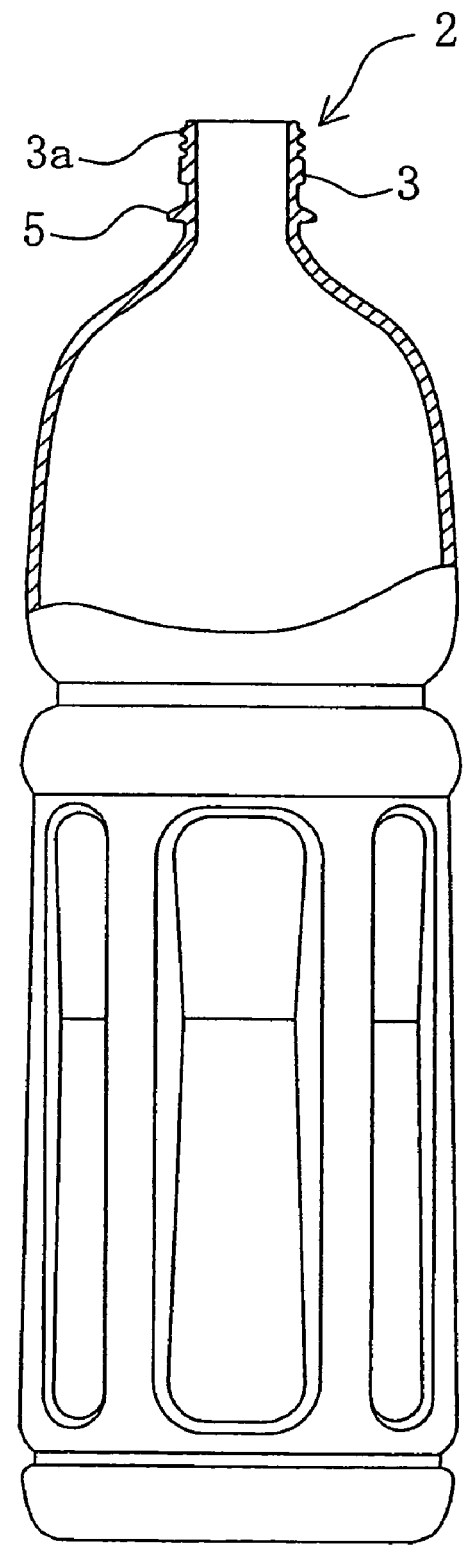

METHOD OF STERILIZATION AND APPARATUS THEREFOR

TECHNICAL FIELD

The present invention relates to a method and a system for sterilizing various concave articles such as vessels made of various materials including synthetic resins, paper and the like, and preforms for PET (polyethylene terephthalate) bottles.

BACKGROUND ART

It is the conventional practice to sterilize in advance the interior of bottles and other vessels upon filling them with contents. Patent Document 1 (JP2001-39414A) discloses sterilizing the interior of a blow-molded bottle by introducing mist of a sterilizing agent into the bottle. Patent Document 2 (JP2000-326935A) discloses sterilizing the interior of a preform by dripping the preform into a germicidal solution before blow molding.

SUMMARY OF INVENTION

According to the sterilizing process disclosed in Patent Document 1, the manufacturer of bottles (made of PET or the like) sterilizes blow-molded bottles which are then transported to the user, and the user keeps these bottles in a storage warehouse until contents are charged. In the sterilizing process disclosed in Patent Document 2, in contrast, the manufacture sterilizes the preforms each having a small volume in advance of the blow molding thereof and conveys the sterilized preforms to the user, and the user keeps the preforms in a storage warehouse until contents are charged. The latter sterilizing method is therefore more convenient in transportation and storage of the vessels. Therefore, the latter sterilizing process has been adopted recently in an increasing number of cases than the former. In some cases where the both methods are used jointly, the sterilization is applied at the preform stage and further at the bottle stage. This practice provides an advantage of reducing the amount of mist sprayed in the bottle.

The sterilizing process disclosed in Patent Document 2, while bringing about many advantages in transportation and storage of vessels as described above, has still room for further development in control of the volume and the concentration of the liquid germicide.

It is therefore an object of the present invention to provide a process and a system capable of more efficient sterilization as compared with the conventional techniques.

To achieve the above mentioned object, the first aspect of the present invention provides a sterilizing process comprising the steps of measuring a liquid germicide, injecting the measured liquid germicide into hollows of concave articles (1), discriminating the more or less of volume of the liquid germicide from the injected liquid germicide, storing only the concave articles (1) which each have a proper volume of the liquid germicide into a storage (6), thereafter closing the storage (6), and leaving the concave articles to stand in the closed storage for a prescribed time period.

According to this first aspect of the present invention, the measured liquid germicide is injected into hollows of the concave articles (1), and acceptability of volume is determined from the injected liquid germicide. It is therefore possible to cause a proper volume of the liquid germicide to attach to the concave articles (1) such as vessels or preforms, therefore, to sterilize efficiently the interior of article within the storage (6), and to prevent the occurrence of incomplete sterilization.

The second aspect of the present invention adopts, in the sterilizing process according to the first aspect, a sterilizing process further comprising the step of determining acceptability of the volume of injected liquid germicide by taking a photograph of the injected liquid germicide.

According to the second aspect of the invention, in which the injected liquid germicide is photographed, and acceptability of the volume of injected liquid germicide is determined from the photograph thus taken, the volume of injection can be accurately detected without disturbing the injection of the liquid germicide.

The third aspect of the present invention adopts, in the sterilizing process according to the first or second aspect, a sterilizing process of injecting the liquid germicide toward a side wall of the inner surface of the concave article (1).

According to the third aspect of the invention, in which the liquid germicide attaches to the inner side wall of the concave article (1) and falls along the side wall, the liquid germicide attaches in so much wider area of the hollow of the concave article, thus improving the sterilizing effect.

The fourth aspect of the present invention adopts a sterilizing system comprising a conveying means (7) which conveys concave article (1); an injection means (8) which measures a liquid germicide and sprays it into a hollow of the concave article (1) during the conveyance; a germicide feeding means (12) which feeds the liquid germicide to the injection means (8); a liquid volume discriminating means (9) which takes a photograph of the liquid germicide ejected from the injection device (8) to determine acceptability of the liquid volume; and a storage (6) which is to enclose the concave article (1) which has the liquid germicide attached therein.

According to the fourth aspect of the invention, it is possible to inject the liquid germicide fed from the germicide feeding means (12) into hollows of the concave articles (1) through the injection means (8) after measuring, so that the liquid germicide attaches with a constant volume to every concave article (1) transported by the conveying means (7) continuously, and then to store the articles into the storage (6). Since acceptability of the liquid volume is determined by taking a photograph of the liquid germicide after injection, it is possible to more closely control the volume of adhering liquid germicide, and store only the concave articles (1) which each have a proper volume of the liquid germicide into the storage (6). This permits an efficient sterilization of a large number of concave articles (1), thus eliminating the risk of incomplete sterilization.

The fifth aspect of the present invention adopts, in the sterilizing system according to the fourth aspect of the invention, a sterilizing system in which, upon detection of unintended discharge of the liquid germicide by the liquid volume discriminating means (9), the conveyance of the concave article (1) by the conveying means (7) is suspended.

According to the fifth aspect of the invention, it is possible to prevent the concave articles (1) from receiving an excessive volume of the liquid germicide caused by the unintended discharge of the liquid germicide, and to prevent the conveying line from contaminating with the liquid germicide.

The sixth aspect of the present invention adopts, in the sterilizing system according to the fourth aspect of the invention, a sterilizing system in which, upon detection of non-injection of the liquid germicide onto the concave article (1) by the liquid volume discriminating means (9), the concave article (1) is excluded from the conveying means (7).

According to the sixth aspect of the invention, the concave article (1) to which the liquid germicide has not been supplied and which would fall into incomplete sterilization is excluded from the conveying means (7). The mixing of the incomplete sterilized concave article (1) in the storage is prevented. Since the conveying means (7) continues to run, the sterilization operation can be sustained.

The seventh aspect of the present invention adopts, in the sterilizing system according to the fourth aspect of the invention, the sterilizing system is provided with a concentration determining means (28) for determining acceptability of concentration of the liquid germicide fed into the injection means (8).

According to the seventh aspect of the invention, in which the liquid germicide having the necessary concentration for sterilization can be injected to the concave article (1) a proper sterilization can be sustained.

The eighth aspect of the present invention adopts, in the sterilizing system according to the seventh aspect of the invention, a sterilizing system in which, upon detection of a defective concentration of the liquid germicide by the concentration determining means (28), the conveyance of the concave article (1) by the conveying means (7) is suspended.

According to the eighth aspect of the invention, large outbreaks of the defectively sterilized concave articles (1) can be prevented.

BRIEF DESCRIPTION OF THE DRAWINGS

FIG. 1(A) is a vertical sectional view illustrating a preform sterilizable by the sterilizing process and system of the present invention; and FIG. 1(B) is a partially cutaway elevational view of a bottle obtained by blow-molding this preform;

BEST MODE FOR CARRYING OUT THE INVENTION

Figure 2:
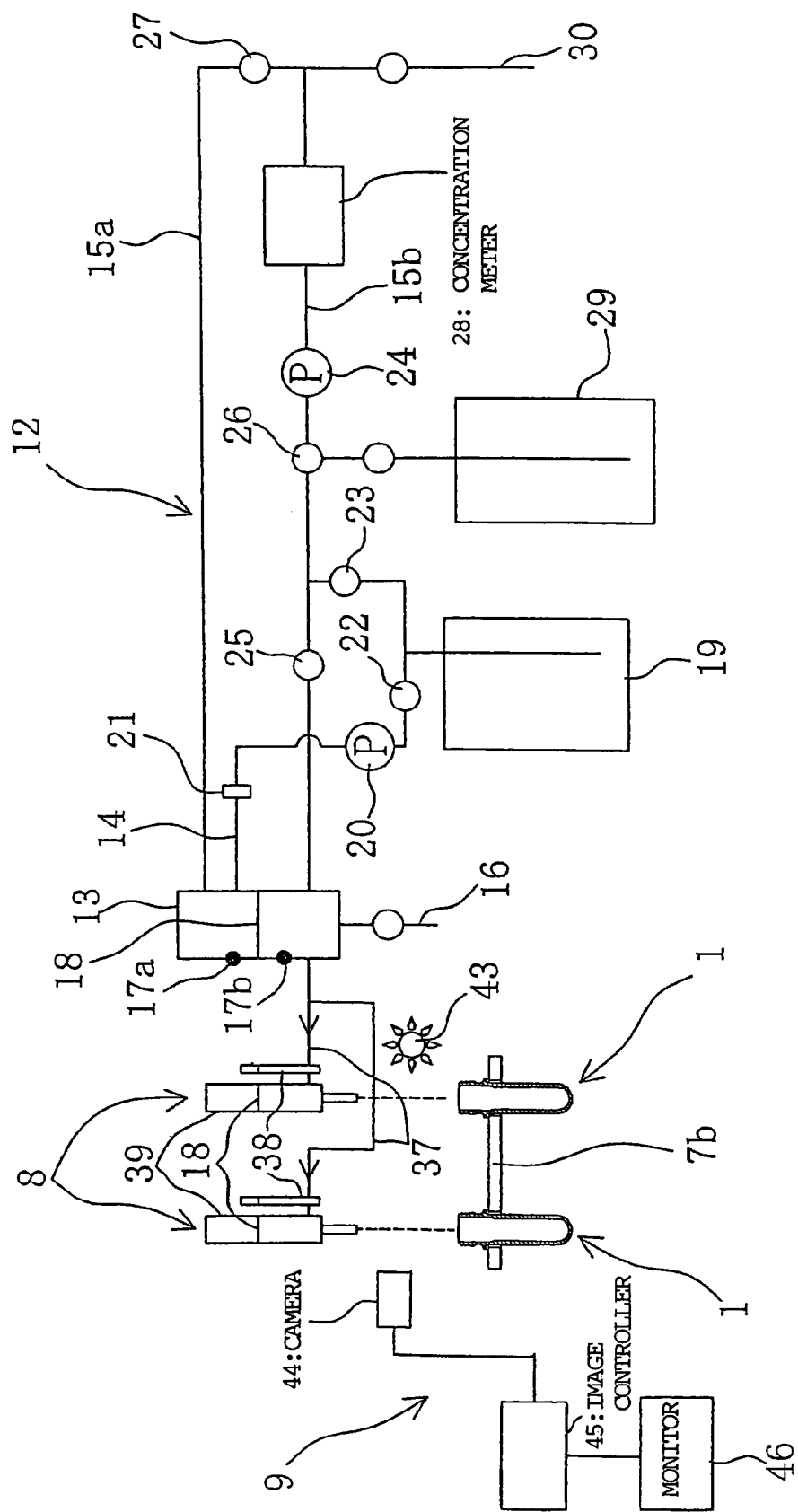
FIG. 2 is an elevational view schematically illustrating the sterilizing system of the present invention.

Now, some embodiments of the present invention will be described with reference to the drawings.

First Embodiment

In this embodiment, a preform 1 shown in FIG. 1(A) serves as a concave article which is an object of sterilization. According to the sterilizing process and system of the present invention, the object to be sterilized is not limited to the preform 1, but a bottle 2 shown in FIG. 1(B) obtained by blow-molding the preform 1, and storages formed from various materials into various shapes are also included.

The preform 1 has a concave shape as a whole as shown in FIG. 1(A), and comprises a lip part 3 having a male thread 3a, a closed-bottom cylindrical barrel part 4 which is extended to the lip part 3, and a flange part 5 formed at the lower end of the lip part 3. The preform 1 is integrally molded by the injection-molding of, for example, polyethylene terephthalate (PET). The injection-molded preform 1 undergoes the injection of a liquid germicide as described later, and then it is put in a storage, transported, and stored. Then, the closed-bottom cylindrical barrel port 4 is blow-molded so as to shape a bottle 2 having a larger volume as shown in FIG. 1(B). Next, the bottle 2 is filled with contents, and is stamp-capped with a cap or the like not shown.

Figure 3:
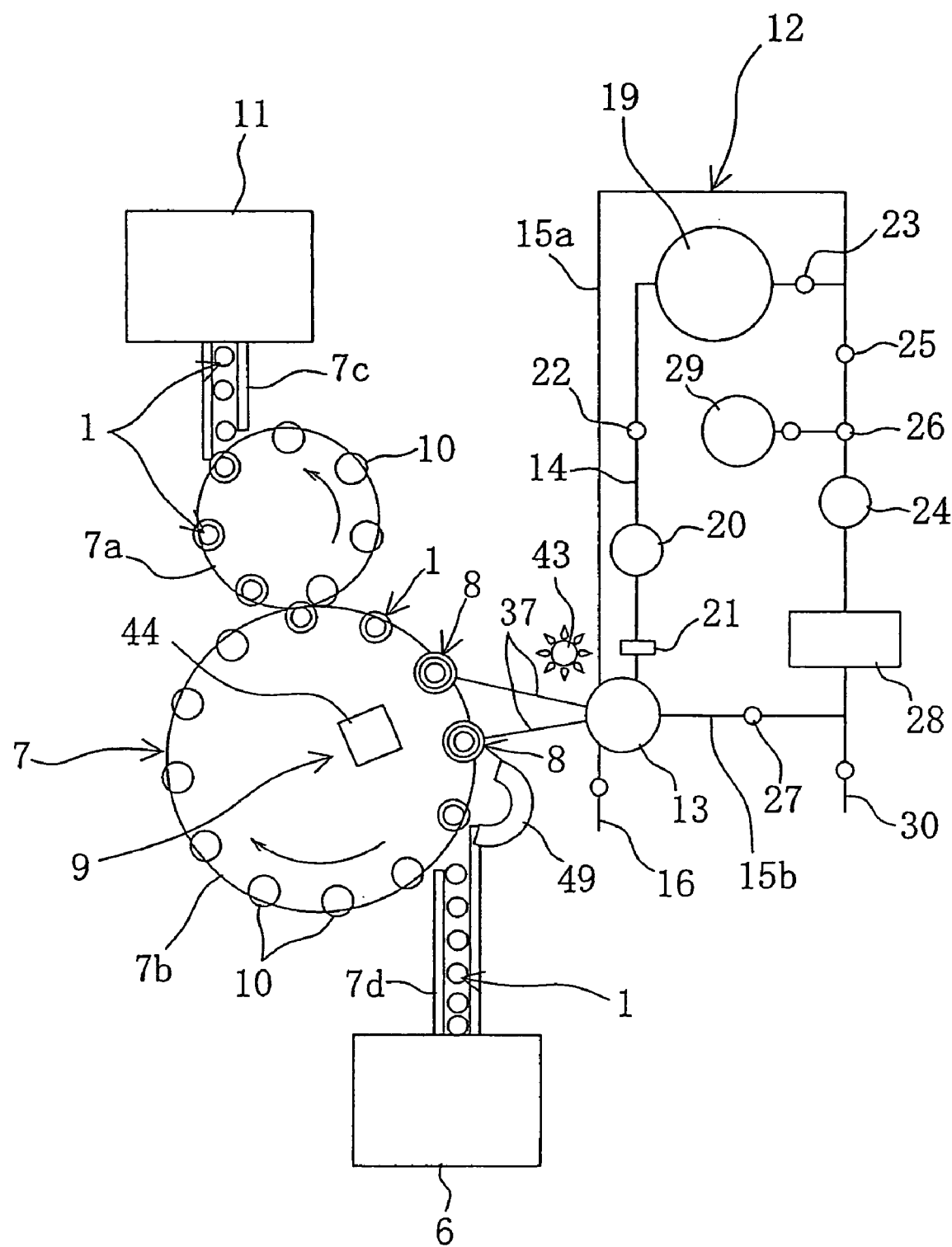
FIG. 3 is a plan view schematically illustrating the sterilizing system of the present invention.

The system for sterilizing the preform 1 has a configuration as shown in FIGS. 2 and 3, and it performs the functions of measuring a liquid germicide; injecting the measured liquid germicide into hollows of the preforms 1; discriminating the more or less of volume of the liquid germicide from the injected liquid germicide; storing only the preforms 1 which each have a proper volume of the liquid germicide adhering thereto into a container 6 as the storage; closing the container 6; and leaving the preforms to stand in the container for a prescribed time period.

The liquid germicide to be used is, for example, an hydrogen peroxide aqueous solution diluted with a volatile solvent. The concentration of hydrogen peroxide in the liquid germicide is adjusted to, for example, a value within a range of from 0.1 to 10% by weight. Applicable solvents include ethyl alcohol, methyl alcohol, acetone, isopropyl alcohol and any mixed solvents prepared by mixing a plural kinds of solvents. While hydrogen peroxide aqueous solution can be singly used as the liquid germicide, it is desirable to dilute it with the volatile solvent so that the hydrogen peroxide aqueous solution can take the form of thin film which would be quickly spread over the inner surface of the preform 1. Thus, the evaporation of hydrogen peroxide can be accelerated, and the time required for sterilizing the inner surface of the concave preform can be shortened.

Concretely, the sterilizing system comprises, as shown in FIGS. 2 and 3, a conveyor 7 which is a means for conveying the preform 1 as the concave article; an injector 8 which is a means for injecting the measured liquid germicide into hollows of the preform 1 in conveyance; a liquid germicide feeding apparatus 12 which is a means for feeding the liquid germicide to the injector 8; a liquid volume discriminating device 9 which is a means for determining acceptability of the liquid volume by taking a photograph of the liquid germicide injected from the injector 8; and a container 6 which encloses the preforms 1 having the liquid germicide attached thereto.

The conveyor 7 has a plurality of turntables 7a and 7b. Each of the turntables 7a and 7b has clamps 10 for clamping a plurality of preforms 1 around the turntable at equal intervals so that the neighboring turntables 7a and 7b hand over the preforms 1 between their clamps while rotating at the same peripheral speed. For example, an injection molding machine 11 is connected to the upstream-side turntable 7a via a feeding conveyor 7c. The preforms 1 injection-molded by the injection molding machine 11 are delivered through the feeding conveyor 7c to the clamps 10 of the turntable 7a. When the injection molding machine 11 is located on a separate place, many injection-molded preforms 1 are transported by a container or the like not shown to the entrance of the feeding conveyor 7c, and delivered through the feeding conveyor 7c to the turntable 7a. The container 6 as the storage is connected to the downstream-side turntable 7b via a discharge conveyor 7d. The preforms 1 which take the injection of the liquid germicide from the injector 8 while being conveyed on the downstream-side turntable 7b are discharged to the discharge conveyor 7d from the turntable 7b. The discharge conveyor 7d throws the preforms 1 into the container 6. The turntables 7a and 7b are set to feed the preforms intermittently at regular intervals so as to effect an accurate delivery of preforms. However, continuous feed is also possible.

The liquid germicide feeding apparatus 12 is equipped with a cushion tank 13. The cushion tank 13 is a tank elongated to the vertical direction, to which an import pipe 14, circulation pipes 15a and 15b, a drainpipe 16 and the like for the liquid germicide are connected. An upper-level sensor 17a and a lower-level sensor 17b are attached to the inner side of the cushion tank 13, and the influent rate of the liquid germicide is controlled so that the liquid level 18 of the liquid germicide is maintained between the upper and lower-level sensors 17a and 17b.

The import pipe 14 has an end extending from a liquid germicide reservoir tank 19 to the cushion tank 13 and the other end connected to the circulation pipe 15b. A feed pump 20, a filter 21, and valves 22 and 23 are provided in the import pipe 14. The circulation pipes 15a and 15b are annularly connected to the cushion pipe 13. A circulation pump 24, various valves 25, 26 and 27, and a concentration meter 28 are provided in the circulation pipes 15a and 15b, and a solvent reservoir tank 29, a drain pipe 30 and the like are connected thereto.

The concentration meter 28 is a device for measuring the concentration of the liquid germicide, including a device such as a UV densitometer which determines the concentration of the liquid germicide by detecting the ultraviolet rays quantity absorbed in the liquid germicide. The applicable concentration meter is not limited to the UV densitometer, but is also a densitometer of a type which causes absorption of visible light or infrared rays, or a densitometer of a type measuring concentration by detecting the refracted light quantity.

Figure 4:
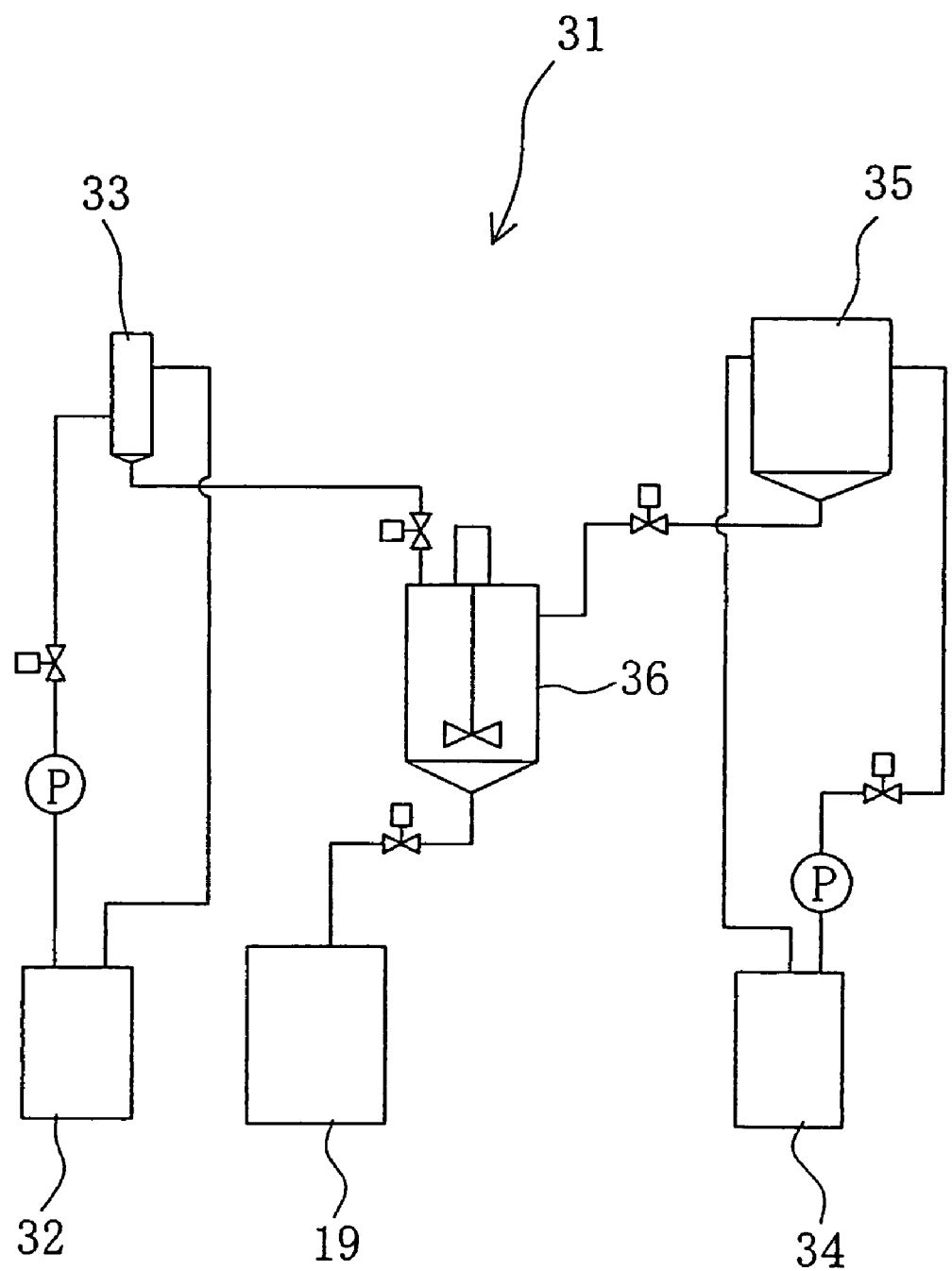
FIG. 4 is a block diagram illustrating a preparation apparatus of a liquid germicide.

A preparation equipment for the liquid germicide is annexed to the liquid germicide feeding apparatus 12. As shown in FIG. 4, the preparation device 31 comprises a germicide reservoir tank 32 storing hydrogen peroxide solution, a germicide measuring tank 33 for measuring the germicide, a solvent reservoir tank 34 which stores a volatile solvent such as ethyl alcohol, a solvent measuring tank 35 which measures the solvent, a mixing tank 36 where the germicide and the solvent are mixed, a liquid germicide reservoir tank 19 which stores the mixed liquid germicide, and a pipeline connecting these tanks. Various valves and pumps are arranged on the pipeline. Through control of the various valves and pumps, a predetermined volume of hydrogen peroxide solution is sent from the germicide reservoir tank 32 to the mixing tank 36 via the germicide measuring tank 33, and a predetermined volume of solvent is sent from the solvent reservoir tank 34 to the mixing tank 36 via the solvent measuring tank 35. Hydrogen peroxide solution and the solvent thus supplied are mixed in the mixing tank 36 to prepare the liquid germicide. The thus prepared liquid germicide is stored in the liquid germicide reservoir tank 19, and the liquid germicide reservoir tank 19 is conveyed to the proximity of the cushion tank 13. Alternatively, the liquid germicide reservoir tank 19 and the cushion tank 13 may directly be connected by piping.

The sterilizing process through this liquid germicide feeding apparatus will be carried out as described below.

Prior to starting operation of the sterilizing system, the liquid germicide exchange process in the sterilizing system is carried out in the following procedure.

The valves of the cushion tank 13 and of drainpipes 16 of the circulation pipes 15a and 15b are opened, and the liquid germicide used in the preceding operation is wholly discharged.

Then, the concentration meter 28 is set at the zero level while the valve 26 from the solvent reservoir tank 29 is turned over, and the circulation pump 24 is made to run so as to discharge the solvent from the valve 30.

Upon setting the concentration meter at the zero level, the concentration of the liquid germicide is measured while the valve 26 is turned over so as to discharge the liquid germicide from the valve 30. If the concentration is out of the prescribed range, an alarm is sounded by a signal from the concentration meter 28. As a result, the exchange process of the liquid germicide is stopped. The liquid germicide is prepared again, and the concentration meter 28 is set again at the zero level.

Upon confirmation of a normal concentration of the prepared liquid germicide, the valves 16 and 30 are turned off, and the whole piping is filled with the liquid germicide by operating the feed pump 20. The feed pump 20 is stopped at the moment when the liquid level 18 in the cushion tank 13 reaches the upper-level sensor 17a.

This causes completion of the liquid germicide exchange process, making the sterilizing step operable.

At the start of the sterilizing step, the valve 23 is turned off, and the liquid germicide in the cushion tank 13 is circulated by means of the circulation pump 24 through the circulation pipe 15a, the concentration meter 28, and the circulation pipe 15b. The concentration of the liquid germicide is always monitored by the concentration meter 28 during the sterilizing step. When the concentration of the liquid germicide comes to be out of the prescribed range, an alarm is sounded in response to the signal from the concentration meter 28. When an abnormal concentration is detected, the operation of the sterilizing system is stopped, and the liquid germicide is prepared again. The concentration meter 28 is set at the zero level again.

During the sterilizing step, when the liquid germicide is consumed and the liquid level in the cushion tank 13 reaches the lower-level sensor 17b, the feed pump 20 is made to run so that the cushion tank 13 is fed with the liquid germicide until the liquid level 18 reaches the upper-level sensor 17a.

The injector 8 measures the liquid germicide in cooperation with the cushion tank 13. More specifically, as shown in FIGS. 2 and 3, the injector 8 is connected to the cushion tank 13 through a conduit 37 for the liquid germicide, and the injector 8 is charged with the liquid germicide up to the same liquid level 18 as that of the liquid germicide in the cushion tank 13. A level gage 38 is equipped to the injector 8 so as to permit monitoring of the liquid level of the liquid germicide from outside the injector 8. In the figure shown, two injectors 8 is arranged so as to face two preform 1 in the longitudinal direction on the turntable 7b. Of course, it is possible that only one injector 8 may be arranged so as to face one preform 1, or three or more injectors may be arranged so as to face three or more preforms 1.

Figure 5:
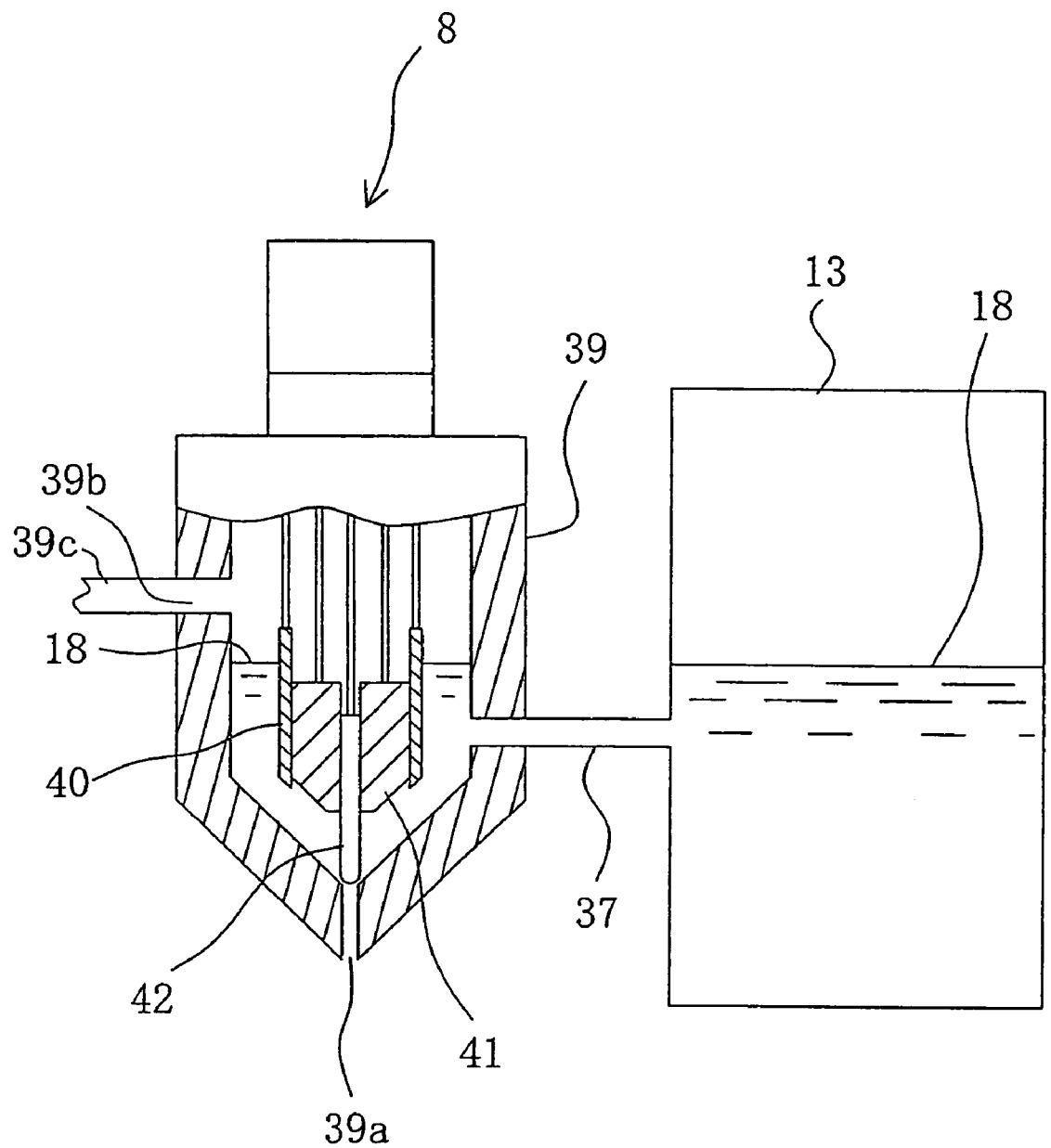
FIG. 5 is a vertical sectional view of an injector.

This injector 8 is an apparatus which measures the liquid germicide which is charged in the injector up to a certain volume at the same liquid level as in the cushion tank 13, and ejects the liquid germicide in a certain direction, and which has a cylinder 39 having a nozzle 39a at the leading end thereof, as shown in FIG. 5. A conduit 37 from the cushion tank 13 is connected to the cylinder 39, and an opening 39*b* for overflow is provided at a position above the connecting part of the conduit 37.

A pipe 39*c* is provided to the overflow opening 39*b* so as to prevent the overflowing liquid germicide from flowing along the outer wall of the cylinder 39 toward the preform 1.

A cylindrical measuring valve 40 which takes a prescribed volume of liquid germicide in the cylinder 39, a plunger 41 slidable within the measuring valve 40, and a needle valve 42 slidable along the center of the plunger 41 so as to face to the nozzle 39*a* are provided in the cylinder 39. The measuring valve 40, the plunger 41 and the needle valve 42 are individually driven by air cylinder devices which are not shown and use a working fluid such as air. Driving method is not limited to that by the working fluid, but is also capable of using any methods based on a servo-motor or the like.

Figures 6A, 6B, 6C:
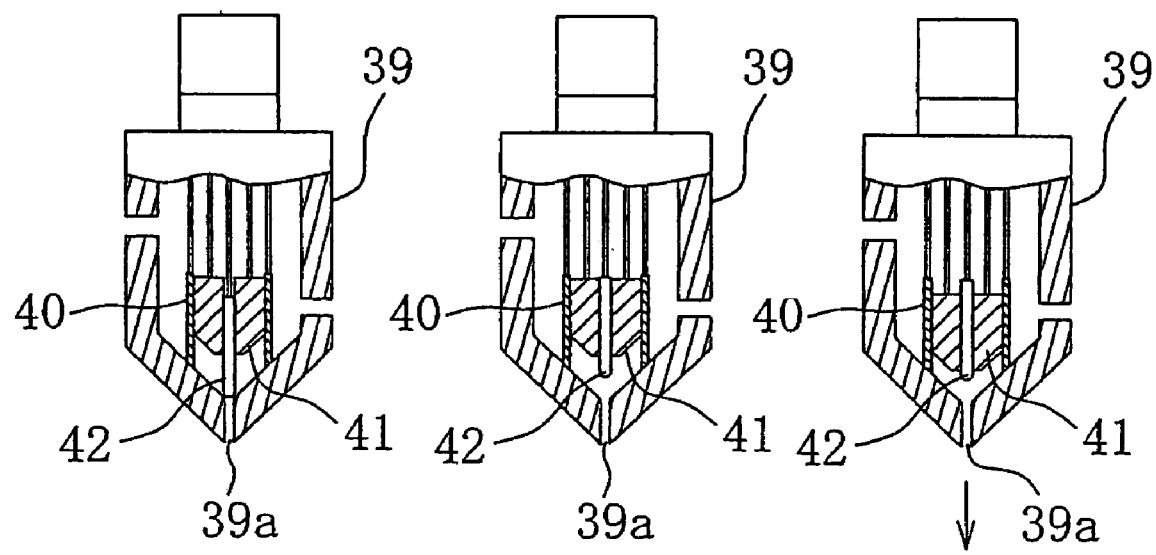
FIG. 6 is a descriptive view of operation of the injector.
Figures 6D, 6E, 6F:
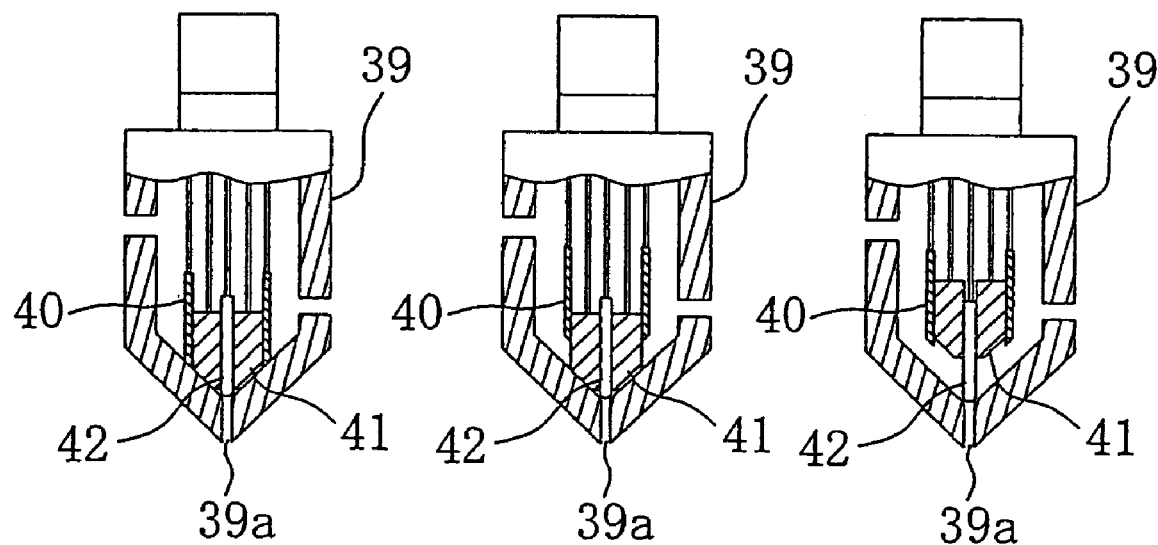

The injector 8 acts as shown in FIG. 6, and when a preform 1 is brought to the position below the nozzle 39*a*, the injector 8 ejects the liquid germicide of a prescribed volume toward the opening of the cavity of the preform. First, as shown in FIG. 5, the measuring valve 40 descends toward the nozzle 39*a* side in order to measure and capture the liquid germicide of the prescribed volume (FIG. 6A); then, the needle valve 42 ascends in order to open the nozzle 39*a* (FIG. 6B); and the plunger 41 comes down to cause ejection of the liquid germicide from the nozzle 39*a* in the direction of the arrow (FIG. 6C). Although the amount of the liquid germicide to be ejected can be varied by the volume, the inner surface area and the like of the preform 1, it may be, in general, a prescribed volume within the range from about 0.5 to 100 μ•. After the ejection of the liquid germicide toward the preform 1, the needle valve 42 descends to close the nozzle 39*a* (FIG. 6D), and then the measuring valve 40 ascends (FIG. 6E). Finally, the plunger 41 rises up (FIG. 6F) in order to be followed by the influent of the liquid germicide from the cushion tank 13 to the cylinder 39. These motions are repeated for each preform 1, and the liquid germicide in a measured amount is injected into the individual preforms 1.

The injection device of the liquid germicide is not limited to that shown here, but is capable of using any other injecting method as far as the injection device has an injecting rate capable of answering the production capacity of the line and keeps the injection volume stable.

Figure 7A:
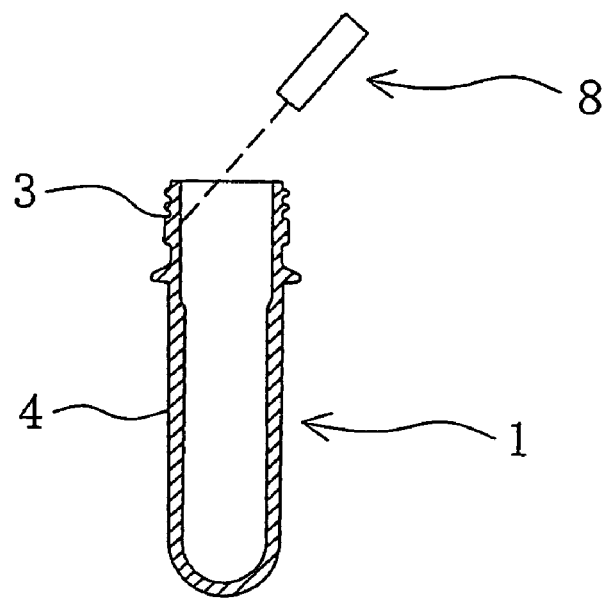
FIG. 7 is a descriptive view illustrating the positional relationship between the injector and the preform.

The injector 8 may be arranged so that the axial center thereof is on the extension of the axial center of the preform 1, but preferably be arranged so that the axial center is inclined relative to the preform 1 on the conveyor 7 and the axial centers thus cross each other as shown in FIG. 7(A). As a result, the injected liquid germicide attaches to the inner surface of the barrel part 4 or lip part 3 which are the sidewall of the preform 1 and falls along the inner surface of the side wall. The liquid germicide attaches to so much larger area of the cavity in the preform, i.e., the concave article, which is followed by leading to an improved sterilizing effect.

The liquid volume discriminating device 9 serves to determine acceptability of the injection volume by taking a photograph of the liquid germicide ejected from the injector 8. As shown in FIGS. 2 and 3, the device is provided with a lamp 43 illuminating the liquid germicide discharged from the nozzle 39*a* of the injector 8, and a camera 44 taking a photograph of the discharged liquid germicide.

Figure 8A:
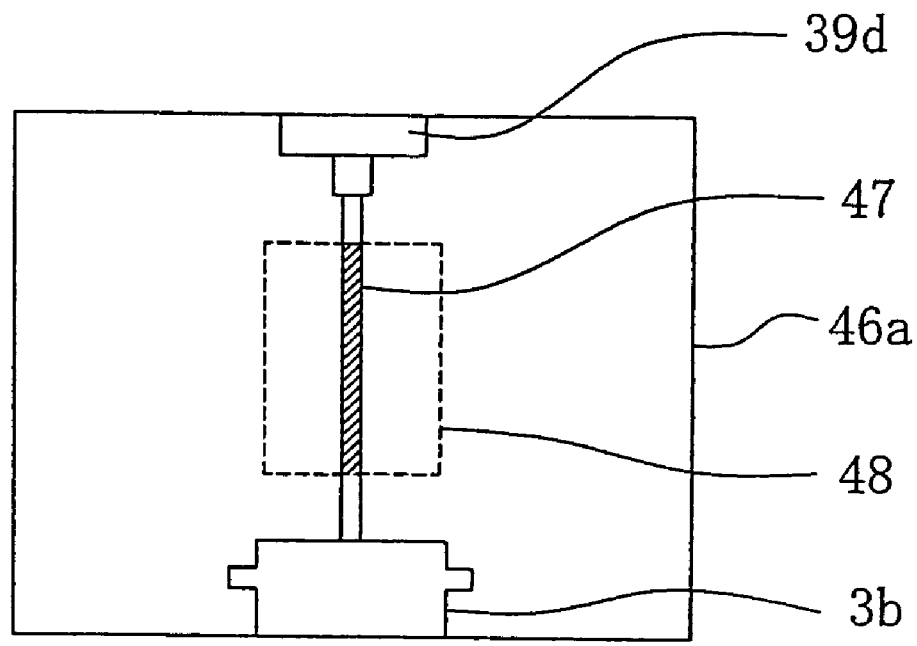
FIG. 8 illustrates a monitor screen of a liquid volume discriminating device.

The camera 44 is for example a CCD camera, and takes a photograph of the liquid germicide illuminated by the lamp 43. The image taken by the camera 44 is displayed on a monitor 46 via an image controller 45. As shown in FIG. 8(A), an image 39*b* of the nozzle 39*a* of the injector 8, an image 47 of the liquid germicide ejected linearly from the nozzle 39*a*, and an image 3*b* of the lip part 3 of the preform 1 are displayed on the screen 46*a* of the monitor 46.

The liquid volume discriminating device 9 cuts off the portion of the image 47 for the liquid germicide by a window 48, and determines the presence or absence of the liquid germicide at a timing when the preform 1 becomes directly below the injector 8. If the absence of the liquid germicide is detected at the timing, the device 9 issues a signal to announce the occurrence of defective sterilization. The liquid volume discriminating device 9 counts the number of pixels in the image 47 of the liquid germicide within the window 48. If the counted number is larger or smaller than a prescribed number of pixels set in advance, the device issues a signal of defective sterilization.

As shown in FIG. 3, a rejecter 49 for removing the defectively-sterilized preform 1 is provided on the turntable 7*b*. Upon receipt of a signal of defective sterilization, the rejecter 49 takes the corresponding preforms 1 away from the turntable 7*b*. The shown rejecter 49 is an equipment of the type which widens the clamp 10 on the turntable 7*b* in order to allow the preform 1 to fall down under the turntable 7*b*. The rejecter 49 may be the type of blowing off the preform 1 by air-blow, or the type of disengaging a trap plate which is used for supporting the preform 1.

Figure 8B:
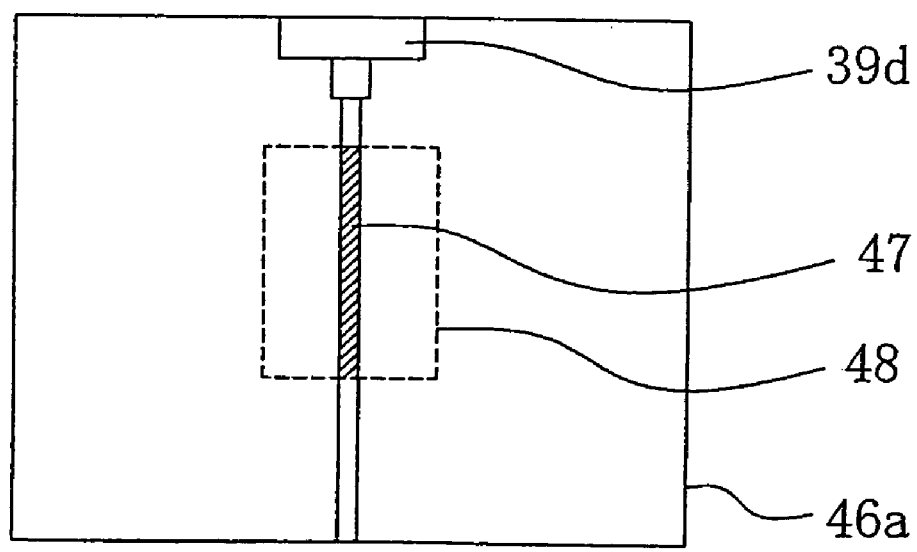

When the liquid volume discriminating device 9 detects the presence of an image 47 of the liquid germicide at a timing other than the timing for conveying the concave preform 1 by the turntables 7*a* and 7*b* as the conveying means 7, the liquid volume discriminating device 9 deems it as representing a state of unintended discharge of the liquid germicide, and issues a signal for suspending the work of the turntables 7*a* and 7*b*. More specifically, as shown in FIG. 8(B), when the image 47 of the liquid germicide is detected between a preform 1 and the following preform 1 being conveyed, the liquid volume discriminating device 9 deems it as representing occurrence of unintended discharge of the liquid germicide from the injector 8, and issues a conveyance stopping signal. This can bring the feeding state of the liquid germicide rehabilitating. Therefore, it is possible to prevent the concave articles 1 from receiving an excessive volume of the liquid germicide, and to prevent the conveying line from contaminating with the liquid germicide.

When the number of pixels of the image 47 of the liquid germicide counted at a timing for conveying the preform 1 as the concave article by the turntables 7*a* and 7*b* as the conveying means 7 is detected as being out of the prescribed range, the liquid volume discriminating device 9 deems it as suggesting the fact that the liquid germicide has not been injected, and issues a signal of defective sterilization. The rejecter 49 excludes the corresponding preforms 1 from the turntable 7*b*, while the turntables 7*a* and 7*b* continue to drive. As a result, it is possible to prevent the defectively sterilized preforms from storing in the storage together with the successfully sterilized preforms.

The storage may take the form, for example, of a lidded container 6, and the preforms 1 which each have the liquid germicide attached thereto in a proper amount with a proper concentration, and which are discharged from the discharge conveyor 7*d* are thrown into the container 6. The container 6 is equipped therein with a bag made of a synthetic resin and being in the inflated state, and the preforms 1 are thrown into the bag. When a prescribed number of preforms 1 accumulate in the bag, the bag is closed and conveyed out, together with the container 6, from the sterilizing system. The closed container 6 is subsequently transported and stored. In the meantime, the liquid germicide is evaporated in each preform in the bag in the container 6 to sterilize the interior of the preforms 1. The container is opened after aging as described above. Sterilized preforms 1 are taken out from the bag in the container 6, sent to the blow molding machine (not shown), and molded into bottles 2. The storage may be the container 6 or a box used singly, or may be a bag used singly so far as it is possible to close the opening thereof. As the method of closing, any various method is acceptable. The various methods include folding the lip part of the bag, heat-sealing the bag, and nipping the bag with a clip.

The operation of the sterilizing system having the above-mentioned configuration will now be described.

The preforms 1 injection-molded by the injection molding machine 11 are fed from the feeding conveyor 7c to the turntable 7b on the downstream side via the turntable 7a on the upstream side. The turntable 7b successively receives the preforms 1 while rotating, and conveys the same directly below the injector 8.

The liquid germicide having a prescribed concentration is fed from the germicide feeding apparatus 12 via the cushion tank 13 into the cylinder 39 of the injector 8. The liquid germicide is obtained by mixing hydrogen peroxide solution and a volatile solvent with a prescribed ratio in a preparation device 31. The concentration of the liquid germicide is continuously monitored with the concentration meter 28 in the germicide feeding apparatus 12, which results in the successive feeding of the liquid germicide with a constant concentration to the injector 8.

In the cushion tank 13, the liquid germicide is constantly kept at the prescribed liquid level 18, and the same liquid level of liquid germicide as in the cushion tank 13 is stored in the cylinder 39 of the injector 8. The injector 8 takes in the liquid germicide of the prescribed volume by means of the measuring valve 40 in the cylinder 39. Upon arrival of the preform 1 under the nozzle 39a, the injector 8 activates the needle valve 42 to open the nozzle 39a, and activates the plunger 41 to eject the liquid germicide from the nozzle 39a.

The liquid germicide ejected from the nozzle 39a of the injector 8, which is in a linear shape, is quickly introduced into the cavity of the preform 1. The liquid germicide attaches to the inner surface of the side wall of the preform 1, then falls along the side wall, and thus attaches to a wide range in the cavity of the preform 1.

The liquid volume discriminating device 9 determines acceptability of the injection volume by taking a photograph of the liquid germicide ejected from the injector 8. The image taken by the camera 44 is displayed on a monitor 46 via an image controller 45.

The liquid volume discriminating device 9 cuts off the portion of the image 47 for the liquid germicide on the screen of the monitor 46 by a window 48, and determines the presence or absence of the liquid germicide at a timing when the preform 1 becomes directly below the injector 8. If the absence of the liquid germicide is detected at the timing, the liquid volume discriminating device 9 issues a signal of defective sterilization.

The liquid volume discriminating device 9 counts the number of pixels in an image of the liquid germicide within the window 48. If the counted number is larger or smaller than a prescribed number of pixels set in advance, the device issues a signal of defective sterilization.

The preform 1 which is judged as being defectively sterilized by the liquid volume discriminating device 9 is removed from the turntable 7b when the preform 1 is conveyed by the turntable 7b to the rejector 49.

When the liquid volume discriminating device 9 detects the presence of an image 47 of the liquid germicide at a timing other than the timing for conveying the concave preform 1 by the turntables 7b, the liquid volume discriminating device 9 deems it as representing a state of unintended discharge of the liquid germicide, and issues a signal for suspending the work of the turntables 7a and 7b. Therefore, it is possible to prevent the preforms 1 and the conveying line from contaminating with the liquid germicide.

Further, the concentration of the liquid germicide is successively monitored by the concentration meter 28 throughout the operation of the sterilizing system. When the concentration of the liquid germicide comes to be out of the prescribed range, an alarm is sounded in response to the signal from the concentration meter 28. When an abnormal concentration is detected, the operation of the sterilizing system is stopped, and the liquid germicide is prepared again in order to resume the sterilizing treatment.

The preforms 1 to which the liquid germicide has been injected at a proper concentration and a proper amount are thrown into the bag in the container 6 via the downstream turntable 7b and the discharge conveyor 7d.

When the preforms 1 are accumulated in a prescribed amount in the container 6, the bag in the container is closed, and the container 6 is conveyed out from the sterilizing system.

Subsequently, the container 6 is transported to the user of the preforms or the others, and stored at there. During this transportation and storage, in the bag of the container 6, the liquid germicide evaporates in each preform 1, and vapor of hydrogen peroxide sterilizes the interior of the preform 1. After the completion of such aging of sterilization, the bag in the container is opened, and the sterilized preforms are taken out from the container 6.

The sterilized preform 1 is molded into a bottle 2 by a blow molding machine, and the obtained bottle is filled with the contents under an aseptic atmosphere, given a cap, and delivered as a product.

Second Embodiment

Figure 9:
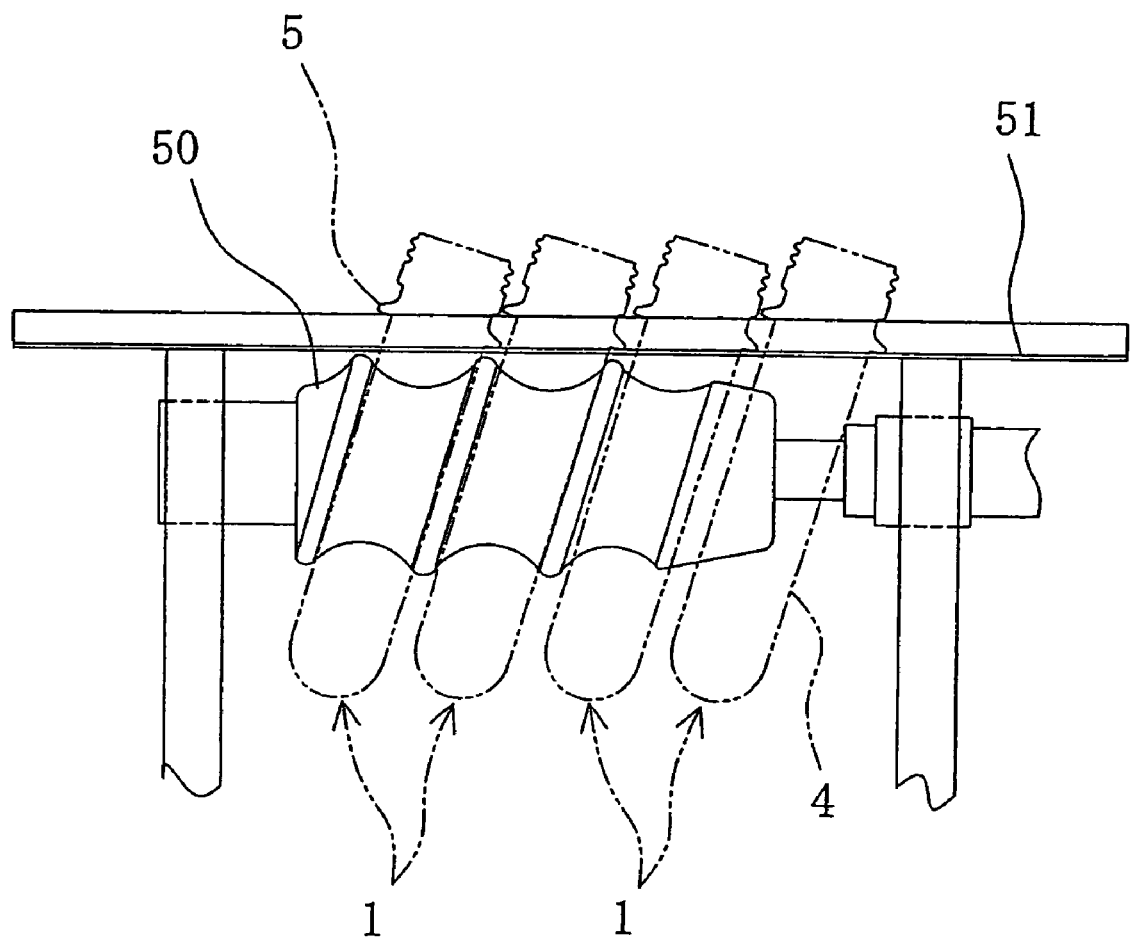
FIG. 9 is an elevational view illustrating another embodiment of the conveyor of the sterilizing system of the present invention.

In this second embodiment, as shown in FIG. 9, a screw conveyor 50 is used as conveying means, while the turntables 7a and 7b are used in the first embodiment. The screw conveyor 50 comprises a pair of screws arranged in parallel, and conveys the preform 1 by holding the barrel 4 of the preform 1 between the screws. A pair of guide rails 51 which are in parallel with each other and in contact with the flange section 5 of the preform 1 are provided above the screws.

Figure 7B:
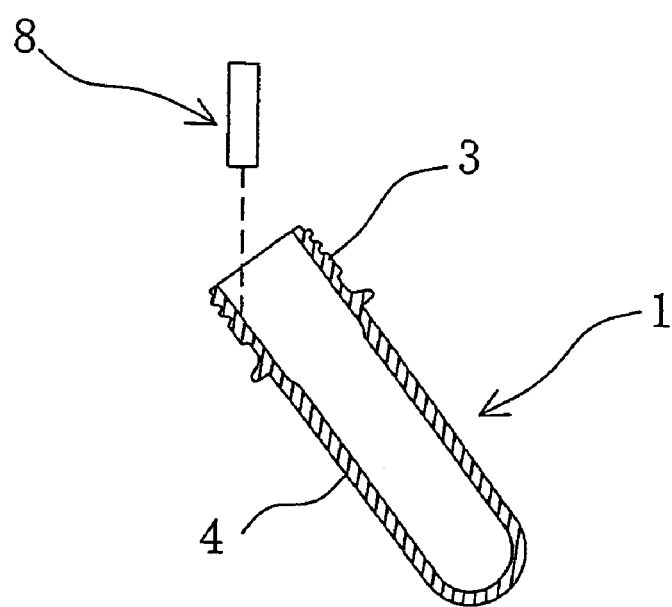

Further, the injector 8 is set above the screw conveyor 50, and which is arranged in the direction of shown in FIG. 7(B). The liquid germicide is ejected from the injector 8 toward the preform 1. While the preform 1 is inclined on the screw conveyor 50, the injector 8 is vertically arranged. As a result, the liquid germicide is injected toward the inner surface of the side wall of the preform 1 as shown in FIG. 7(B).

The invention claimed is:

1. A sterilizing process comprising the steps of measuring a liquid germicide; injecting said measured liquid germicide into hollows of concave articles wherein the volume of the liquid germicide to be injected into said hollows is smaller than the capacity of said hollows of said concave article; discriminating the more or less of volume of the liquid germicide from the injected liquid germicide, wherein acceptability of the volume of injected liquid germicide is determined by taking a photograph of the injected liquid germicide flow; storing only the concave articles which each have a proper volume of the liquid germicide into a storage, then closing the storage, and leaving the concave articles to stand in the closed storage for a prescribed time period.

2. The sterilizing process according to claim 1 wherein said liquid germicide is injected toward a side all of said hollows of the concave article.

3. A sterilizing system comprising a conveying means which conveys the concave article; an injection means which measures a liquid germicide of a volume being smaller than the capacity of the hollow of said concave article, and injects it into a hollow of the concave article during the conveyance; a germicide feeding means which feeds the liquid germicide to the injection means; a liquid volume discriminating means which takes a photograph of the liquid germicide flow ejected from the injection device to determine acceptability of the liquid volume; and a storage which is to enclose the concave article which has the liquid germicide attached therein.

4. The sterilizing system according to claim 3, further comprising a means for detecting unintended discharge of the liquid germicide by the liquid volume discriminating means and suspending conveyance of the concave article upon such detection of unintended discharge of the liquid germicide by the liquid volume discriminating means.

5. The sterilizing system according to claim 3, further comprising a means for detecting non-injection of the liquid germicide onto the concave article by the liquid volume discriminating means and a means for excluding said concave article from the conveying means and excluding said concave article from the conveying means upon such detection of non-injection of the liquid germicide onto the concave article by the liquid volume discriminating means.

6. The sterilizing system according to claim 3, wherein said system is provided with a concentration determining means which determines acceptability of concentration of the liquid germicide fed into the injection means.

7. The sterilizing system according to claim 6, further a means for suspending the conveyance of the concave article by the conveying means upon such detection of a defective concentration of the liquid germicide by the concentration determining means.

* * * * *